United States Patent
Robinson et al.

(10) Patent No.: US 8,101,080 B2
(45) Date of Patent: Jan. 24, 2012

(54) ADVANCED BIOLOGIC WATER TREATMENT USING ALGAE

(75) Inventors: Terry S. Robinson, Corvallis, MT (US); Kevin S. McGraw, Stevensville, MT (US); Jared W. Sylvester, Corvallis, MT (US); Jesse D. Weidow, Pinesdale, MT (US)

(73) Assignee: AlgEvolve, LLC, Corvallis, MT (US)

( * ) Notice: Subject to any disclaimer, the term of this patent is extended or adjusted under 35 U.S.C. 154(b) by 0 days.

(21) Appl. No.: 13/134,967

(22) Filed: Jun. 22, 2011

(65) Prior Publication Data

US 2011/0266215 A1 Nov. 3, 2011

Related U.S. Application Data

(60) Provisional application No. 61/398,350, filed on Jun. 23, 2010.

(51) Int. Cl.
*C02F 3/32* (2006.01)
*C02F 1/32* (2006.01)

(52) U.S. Cl. ... 210/602; 210/623; 210/631; 210/748.11; 210/259

(58) Field of Classification Search ............ 210/602, 210/623, 631, 748.1, 748.11, 252, 259
See application file for complete search history.

(56) References Cited

U.S. PATENT DOCUMENTS

| | | | |
|---|---|---|---|
| 3,598,726 A | 8/1971 | Welch | |
| 4,267,038 A | 5/1981 | Thompson | |
| 5,151,347 A * | 9/1992 | Delente et al. | 435/3 |
| 6,207,047 B1 | 3/2001 | Gothreaux | |
| 6,416,993 B1 | 7/2002 | Wexler | |
| 6,787,035 B2 | 9/2004 | Wang | |
| 6,929,942 B2 | 8/2005 | Moghe | |
| 7,001,519 B2 | 2/2006 | Linden | |
| 7,172,691 B2 | 2/2007 | Dunlop | |
| 7,850,848 B2 | 12/2010 | Limcaco | |
| 2009/0294354 A1 | 12/2009 | Theodore | |
| 2010/0279395 A1 | 11/2010 | Haley | |
| 2011/0023565 A1 * | 2/2011 | Yanik et al. | 71/11 |
| 2011/0143012 A1 * | 6/2011 | Rettenmaier | 426/648 |

FOREIGN PATENT DOCUMENTS

WO WO 2002/072485 9/2002
WO WO 2008/106100 9/2008

OTHER PUBLICATIONS

Gonzalez, C. et al, "Efficient nutrient removal from swine manure in a tubular biofilm photo-bioreactor using algae-bacteria consortia," Water Science & Technology, 2008, 95-102, 58.1, IWA Publishing.

* cited by examiner

*Primary Examiner* — Fred Prince
(74) *Attorney, Agent, or Firm* — Lumen Patent Firm (57) ABSTRACT

An advanced water treatment method processes a continuous flow of water in a sequence of stages including pre-filtering to remove solids, conditioning to adjust pH, blending with a recycled dense microalgae culture, and passing the resulting mixture through an enclosed, environmentally-controlled photobioreactor where nutrients, PCB's, trace metals and other pollutants and regulated compounds are taken up by the algae. The flow from the PBR is separated using cross-flow filtration to produce a treated water flow and a dense microalgae flow that is recycled to the blending stage upstream. Thus, whereas the algae is recycled, the water entering the system is treated by flowing sequentially through the stages of the system, without any recycling or repetition of treatment stages.

14 Claims, 6 Drawing Sheets

ADVANCED BIOLOGIC WATER TREATMENT USING ALGAE

CROSS-REFERENCE TO RELATED APPLICATIONS

This application claims priority from U.S. Provisional Patent Application 61/398,350 filed Jun. 23, 2010, which is incorporated herein by reference.

FIELD OF THE INVENTION

The present invention relates generally to methods and systems for treating water. More specifically, it relates to advanced water treatment using algae or other biological organisms.

BACKGROUND OF THE INVENTION

Municipal and industrial water treatment systems play a crucial role in an environmentally sustainable society. Water treatment in such systems is conventionally divided into three stages: primary, secondary and advanced water treatment. Advanced water treatment is defined herein as including tertiary water treatment, physical-chemical treatment, combined biological-physical treatment, and generally any process designed to produce an effluent of higher quality than normally achieved by secondary treatment processes. Advanced water treatment improves the quality of water prior to reuse or discharge into the environment in order to limit adverse environmental impact and/or comply with governmental regulations or other restrictions. Advanced treatment typically includes, for example, reducing excessive levels of nutrients (such as nitrogen and phosphorus), as well as reducing trace metals (such as selenium and magnesium) and other pollutants and regulated compounds (such as polychlorinated biphenyls, biological oxygen demand, and carbonaceous oxygen demand). The amount of water discharge, and in a growing number of cases re-use, is limited by the quality of the water. Consequently, there is a need for water treatment systems that are capable of producing water that meets regulated discharge or re-use requirements.

One approach to water treatment involves the use of algae or other biological agents such as cyanobacteria to remove or reduce the amounts of nutrients and trace metals. Existing systems of this kind, however, have one or more disadvantages that include:
a) Low flow rates which require a significant physical footprint to treat large volumes of water,
b) Unacceptably high levels of nutrients, metals, or other pollutants in the treated water,
c) Limited light availability/penetration to optimize biological processes,
d) Lack of velocity resulting in bio-film build up,
e) Uncontrolled environments (open ponds/raceways) presenting opportunities for easy contamination or change in water chemistry,
f) Suspended solids buildup due to lack of pre-filtration, and
g) Inability to manage the bioavailability of constituents in the water for removal by the biological agent (algae, cyanobacteria, etc.).

Accordingly, there remains a need for improved techniques for advanced water treatment using algae or other biological organisms.

SUMMARY OF THE INVENTION

In one aspect, a system and method are provided for advanced water treatment. A continuous flow of water is pre-filtered, conditioned, blended with a dense microalgae culture, and passed a single time through an enclosed, controlled photobioreactor (PBR). These interconnected processes are designed to result in nutrient consumption, trace metal removal, and reductions in other pollutants and regulated compounds from the water. The flow from the PBR is separated into a treated water flow, also referred to as the permeate, and a dense microalgae flow, also referred to as the return activated algae (RAA). The permeate is then discharged or re-used. In some instances, and depending on regulatory requirements, prior to discharge or re-use, the permeate may pass through additional polishing and disinfection processes such as ultra-violet disinfection. The RAA flow is returned to the blending stage to treat the upstream conditioned flow. Whereas the algae is recycled in the treatment system, the water is treated by a continuous flow sequentially through the stages of the system, without any recycling or repetition of treatment stages. The system treats the flow as it passes continuously through the sequence of process stages, one time. The system recycles the required amount of algae appropriate to treat the continuous flow passing through the stages. To compensate for overgrowth of algae, a percentage of the RAA flow from the PBR may be harvested or removed as waste activated algae (WAA) in order to maintain suitable algae density in the system. The amount of WAA removal controls the balance of food (nutrients in water) to biomass (algae) in the treatment system. Depending on nutrient and/or trace metal make-up of the water, additional nutrients or trace metals may be added just prior to the blending stage of the treatment process to ensure proper growth of the algae culture.

In another aspect, a method is provided for advanced water treatment that includes the following steps: a) receiving a continuous flow of water; b) pre-filtering the received flow of water to reduce suspended solids; c) conditioning the pre-filtered flow of water, e.g., by adding $CO_2$ to adjust pH of the pre-filtered flow, to increase bio-availability of nutrient constituents in the water as well as to provide a carbon source for subsequent algae photosynthesis in the pre-filtered flow; d) blending in a blending vessel the conditioned flow with a dense live microalgae flow (RAA) to produce a mixture flow; e) passing the mixture flow once through an enclosed tube photobioreactor (PBR) exposed to natural and/or supplemental light so that microalgae in the mixture flow reproduce and take up nutrients and trace metals in the mixture flow; f) continuously separating microalgae from the mixture flow exiting the photobioreactor to produce a treated flow (permeate) and the dense live microalgae flow (RAA); and g) continuously returning the dense live microalgae flow (RAA) to the blending vessel to mix with incoming conditioned effluent and repeating the aforementioned process.

Preferred embodiments of the method may additionally include one or more of the following aspects. Polymers, coagulants or flocculants may be used to remove from the pre-filtered flow total suspended solids or tannins (color) to ensure a proper nutrient mix and light availability for subsequent treatment processes. The pre-filtered flow may also be sterilized with UV irradiation.

Preferred embodiments also may include measuring nutrient levels of the conditioned flow and adding nutrients prior to entering the blending vessel based on the measured nutrient levels to produce desired nutrient levels of the conditioned flow. Similarly, embodiments may include measuring trace metal levels of the conditioned flow and adding trace metals prior to entering the blending vessel based on the measured trace metal levels to produce desired trace metal levels of the conditioned flow.

Embodiments may include measuring pH of the mixture flow in the photobioreactor and adding $CO_2$ to the photobioreactor based on the measured pH. Embodiments may also include measuring an ambient light level near the photobioreactor and exposing the photobioreactor to supplemental light, where the amount of supplemental light is based on the measured ambient light level. Preferably, the supplemental light has a wavelength between 550 and 700 nanometers, or more preferably between 650 and 675 nanometers. Preferably, the duration of time that a given portion of the mixture flow is directly exposed to light while it passes through the blending stage, PBR stage, and separation stage is 40% to 60% of the total time that the given portion of the mixture flow is in the blending, PBR, and separation stages. In preferred embodiments, the dense microalgae (RAA) flow contains phototrophic algae such as, for example, *Spirulina, Nannochloropsis, Scenedesmus*, and/or *Chlamydomonas*.

Embodiments may include measuring turbidity of the mixture flow exiting the photobioreactor and removing a fraction of the flow (WAA) from the mixture flow, where the size of the fraction is based on the measured turbidity and a desired RAA density level. In a preferred embodiment, the fraction removed may be less than 5% of the flow exiting the photobioreactor, or more preferably 3%.

In preferred embodiments, the separating of the microalgae is performed by filtering the mixture flow exiting the photobioreactor using a cross-flow filtration system. Preferably, the cross-flow filtration system is performed under a flow rate that generates a pressure between 20 and 80 pounds per square inch (psi) within the membrane filter. In some embodiments, the treated flow (permeate) may be polished by filtering, or disinfected by UV irradiation. The method may include using a sensory control and data acquisition (SCADA) system to control the enclosed stages of the treatment environment to achieve productive algae growth.

In another aspect, a system for advanced water treatment is provided which implements the treatment process. The system includes a pre-filter for reducing suspended solids from a received flow of water to produce a pre-filtered flow; a conditioning vessel coupled to the pre-filter for increasing bio-availability of nutrient constituents in a pre-filtered flow to produce a conditioned flow; a blending vessel coupled to the conditioning vessel for mixing the conditioned flow with a dense live microalgae flow (RAA) to produce a mixture flow; an enclosed tube photobioreactor (PBR) coupled to the blending vessel for receiving the mixture flow and allowing microalgae in the mixture flow to reproduce and take up nutrients and trace metals in the mixture flow to produce a treated mixture flow; a separation filter (e.g., a cross-flow filter) coupled to the enclosed tube photobioreactor for continuously separating microalgae from the treated mixture flow exiting the photobioreactor to produce a clean water flow (permeate) and the dense live microalgae flow (RAA); and a dense live microalgae flow (RAA) return coupled to the separation filter for continuously returning the dense live microalgae flow (RAA) to the blending vessel.

Preferably, the system includes a $CO_2$ dosing pump coupled to a transit line connecting the pre-filter to the conditioning vessel for injecting $CO_2$ into the pre-filtered flow to achieve a desired pH level, a dosing pump coupled to a transit line connecting the conditioning vessel to the blending vessel for injecting nutrients into the conditioned flow to achieve a desired nutrient level, a dosing pump coupled to a transit line connecting the conditioning vessel to the blending vessel for injecting trace metals into the conditioned flow to achieve a desired trace metal level, and a $CO_2$ dosing pump coupled to the enclosed tube photobioreactor for injecting $CO_2$ into the mixture flow to achieve a desired pH level.

DETAILED DESCRIPTION

Embodiments of the invention provide advanced, algae-based, water treatment technologies to remove nutrients, trace metals, and other pollutants from the water. Unless otherwise qualified, the term "water" in the present document is defined as including wastewater, sewage, as well as natural and industrial effluents. In the exemplary embodiments described below, unique technologies and processes work together in a continuous, controlled, and automated manner that result in clean water for discharge or re-use. A preferred embodiment of the system specifically targets the reduction or removal of nitrogen, phosphorus, total suspended solids (TSS), biological oxygen demand (BOD), carbonaceous biological oxygen demand (CBOD), polychlorinated biphenyl (PCB) and removal of trace metals, such as Iron, Magnesium, and Selenium, and other pollutants and regulated compounds. The system may be modified to target other constituents. It may also provide industrial plant partners with the opportunity for carbon capture. The treatment system may be managed and controlled through a supervisory control and data acquisition system (SCADA).

Figure 1:
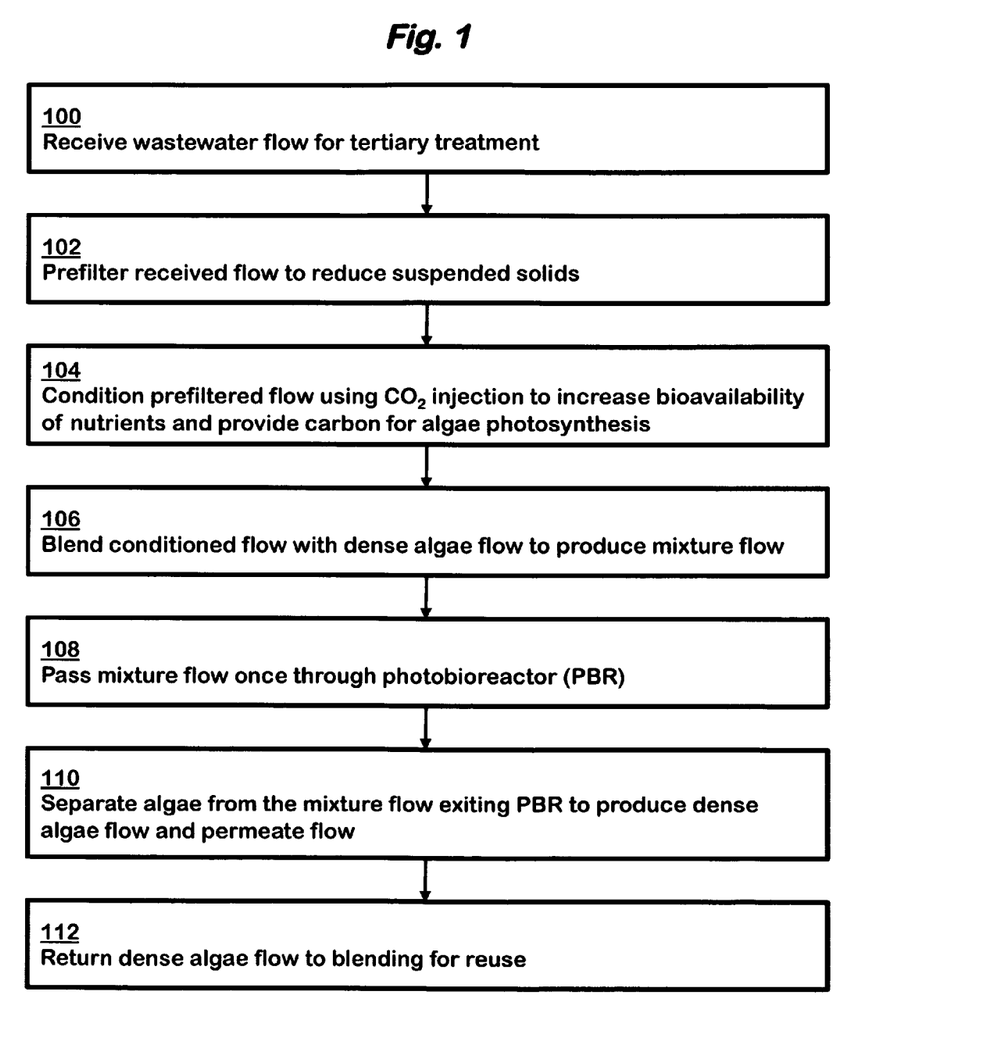
FIG. 1 is an outline of the main steps of a method for advanced water treatment, according to an embodiment of the invention.

An outline of the main steps of the process is shown in the flowchart of FIG. 1. Although presented here as distinct steps, these steps of the treatment process take place concurrently as the flow continuously passes through the sequential stages of the system. In step 100 an advanced water flow is received by the system, for example, from a secondary stage of a water treatment facility. The received flow, if appropriate, may be pre-filtered in step 102 to reduce suspended solids. In some embodiments this step may also include using polymers, coagulants or flocculants to further remove total suspended solids (TSS) and/or tannins (color) to ensure a proper nutrient mix and light availability for subsequent treatment steps. In step 104 the pre-filtered flow is conditioned using $CO_2$ injection to increase the bio-availability of nutrient constituents in the water and also to provide carbon for subsequent algae photosynthesis. The conditioned flow is blended in step 106 with a dense live microalgae flow that is recycled from a later stage in the process. In step 108 the resulting mixture flow is then passed once through a photobioreactor where the microalgae in the mixture reproduce, undergo photosynthesis, and metabolize or bind nutrients and/or trace metals to the algae in the mixture flow. In step 110, the flow exiting the photobioreactor undergoes separation to produce a treated water flow (i.e., permeate) and the dense live microalgae flow, also referred to as a return activated algae (RAA) flow. In step 112, the RAA flow is continuously returned to the blending stage. The interconnected components of the treatment process, following pre-filtration, operate in an environmentally controlled and closed environment to eliminate air-borne contaminants and potential infiltration of unwanted organics. The enclosed environment may be electronically managed using a sensory control and data acquisition (SCADA) system. Environmental controls allow the system to optimize the enclosed environment for productive algae growth.

Figure 2A:
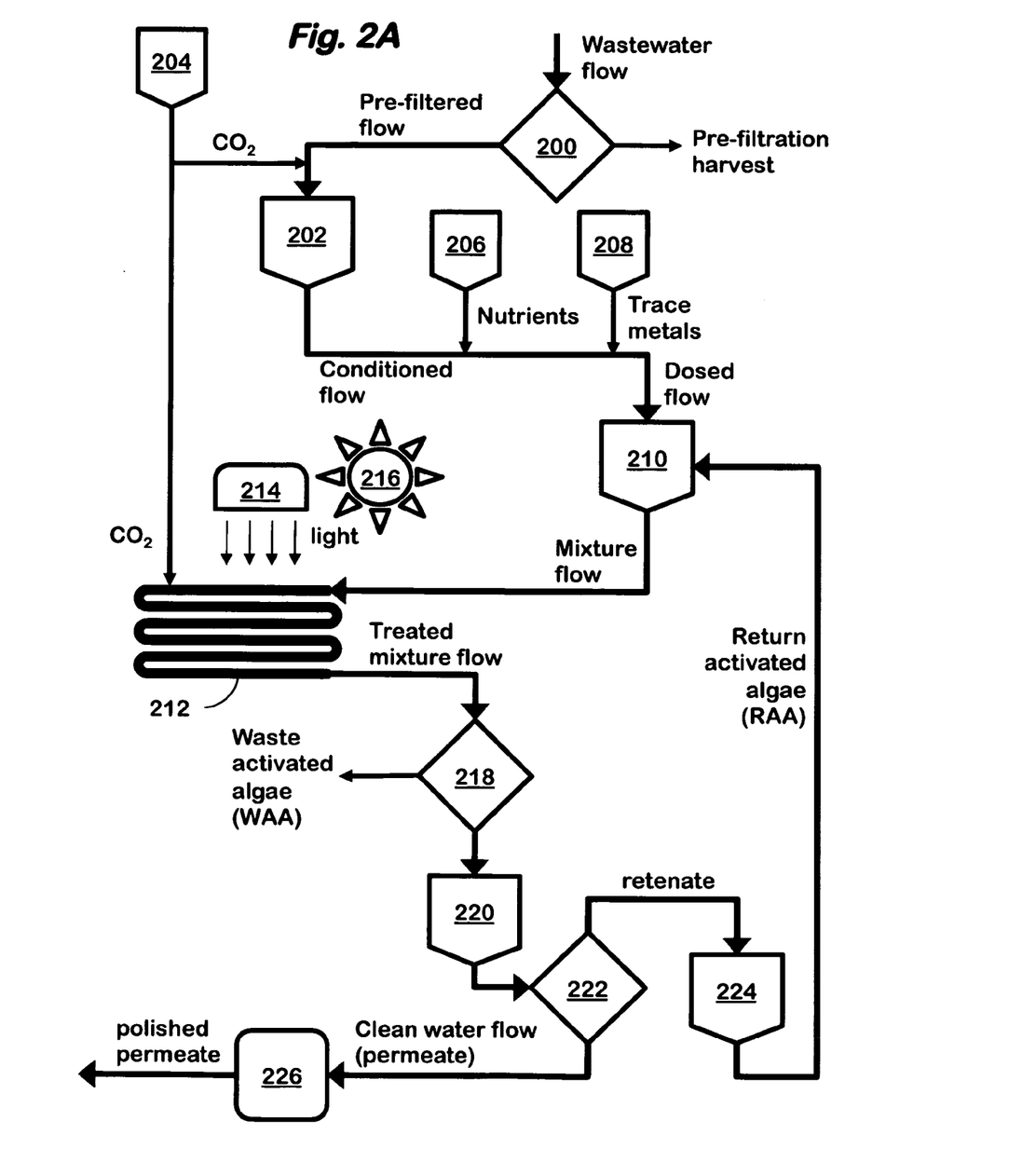
FIG. 2A is a process flow schematic illustrating a system for advanced water treatment, according to an embodiment of the invention.

A preferred embodiment of the method for advanced water treatment will now be described in more detail in relation to the system process flow schematic shown in FIG. 2A.

Stage 1: Pre-Filtration

An incoming water effluent to be treated typically may have some total suspended solids (TSS). Accordingly, in preferred embodiments, the incoming water is initially received by the system at a filtration mechanism 200 which reduces TSS in the received flow. The filtration mechanism 200 may be implemented, for example, as a sand bed filter to remove solids between 5 and 75 micron in size. Optionally, depending on the nature of the received water flow, additional pre-treatment may be implemented using a polymer, coagulant, or flocculant agent to further reduce TSS and/or tannins (color) to improve the performance of later stages of treatment. The addition of these agents, which may be injected in-line or into a tank containing the water effluent, facilitate bonding among suspended solid particulates. The water is slowly mixed and the movement of the water induces particles to collide and clot. Typical hardware used with these pre-treatment agents may include, for example, tanks, automatic dosing systems, a belt filter press and filtration or screens to remove the clots (solids) formed in the process. Solids captured in filtration mechanism 200 are separated from the main flow and harvested.

In addition, in some embodiments, pre-treatment may include passing the flow through an ultraviolet light process to sterilize any biological or viral substances in the water. In alternative embodiments of the invention, pre-filtration may be left out of the process. For example, in circumstances in which the incoming water has limited or no TSS (e.g., less than 15 mg/L) and/or tannins (e.g., less than 250 using the Platinum Cobalt Method), pre-treatment may not be necessary.

Stage 2: Effluent Conditioning

The pre-filtered flow from the filtration mechanism 200 is pumped through a transit pipe to a conditioning vessel 202. In transit, the pH of the pre-filtered flow is monitored and $CO_2$ is injected automatically using a peristaltic dosing pump (or other injection device) 204 to achieve the desired pH level, typically between 5.5 and 6.4. The volume of $CO_2$ injected into the pipe is calculated based on temperature, pH, alkalinity and pressure of the flow. The pH level, prior to and after the injection port, are continuously monitored and pH levels are modified accordingly. Typically, the pH-adjusted flow remains in the conditioning vessel 202 for 30 to 60 minutes. $CO_2$ injection serves two primary purposes: first, it serves to saturate the effluent with dissolved inorganic carbon which the algae require to perform photosynthesis in later stages of the treatment process, as will be describe below. Second, $CO_2$ lowers pH of the flow and thereby dissolves salts which can exist at high pH levels. Lowering the pH and dissolving these salts results in the increased availability of nutrients to algae. For example, if the pH levels are too high, calcium bonds with phosphorus, making the phosphorus less available for algae consumption. Upon exiting the conditioning vessel 202 the conditioned flow has a sufficient bio-availability of nutrients and is carbon rich.

Preferably, the conditioned flow exiting the conditioning vessel 202 is continuously monitored for levels of nutrients and trace metals. In case there is a deficiency of nutrients or metals in the conditioned flow, the conditioned flow is automatically dosed with appropriate amounts of nutrients using peristaltic pump 206 and/or and trace metals using a peristaltic pump 208.

Stage 3: Blending

The conditioned flow (which may be dosed as described above) is pumped through a transit line from the conditioning vessel 202 to a blending tank 210. In addition to receiving the conditioned flow from the conditioning vessel 202, the blending tank 210 also continuously receives a return activated algae (RAA) flow from further downstream in the system, as will be described below. These blended flows are referred to as a mixture flow. The ratio of conditioned flow to RAA flow is a predetermined value selected based on various factors such as system design, nutrient availability, effluent flow rates and retention time. A typical ratio of RAA to conditioned flow is 1 part RAA to 1 part conditioned effluent, or 50/50. This ratio may be maintained in the system, for example, by the use of electronic flow meters, variable frequency drives, pumps and equalization tanks. The algae in the RAA flow may be selected from among various phototrophic algae including, for example, *Spirulina, Nannochloropsis, Scenedesmus*, or *Chlamydomonas*. The blending tank 210 preferably includes a mechanism for creating a turbulent environment sufficient to keep the algae cells in suspension. Turbulence may be maintained, for example, using a cone bottom tank, incoming flow rates, and adjusting the angle of conditioned RAA flow into the tank. The size of the blending tank 210 is predetermined based on system design parameters such as the volume of incoming flow and the retention time required to initiate the nutrient and/or trace metal removal requirements. The retention time in the blending tank 210 is calculated as 50% to 100% of the retention time required in the PBR. A typical retention time, for example, is a value between 30 and 60 minutes. Electronic control systems monitor pH, temperature, and flow rate in the blending tank 210 and these values are used to automatically adjust the retention time using electronic flow meters, variable frequency drives, control valves, and pumps of the mixture flow in the blending tank.

In an alternative embodiment, the conditioning and blending stages described above may be performed in a single integrated stage using a single vessel, tank, or equivalent container. For example, conditioning vessel 202 may be eliminated and the conditioning process described above is performed in the blending tank 210, which serves as the single tank. According to this alternative approach, $CO_2$, nutrients and/or trace metals are injected directly into the single integrated tank, e.g., pumps 206 and 208 are configured to inject directly into tank 210. RAA would be received in the single vessel as described in above and water exiting the single tank would be referred to as the mixture flow.

Stage 4: Nutrient Removal

The mixture flow from blending tank 210 is pumped into a central manifold connected to a photobioreactor (PBR) array 212 preferably composed of multiple PBRs connected in parallel. The manifold distributes the incoming mixture flow equally among the total number of PBRs, e.g., 10. (For simplicity of illustration, a single PBR is shown in the figure.) Each PBR includes a collection of clear (i.e., optically transparent) PVC pipes, each having a diameter preferably between 2 to 6 inches and a length from 20 to 80 feet. The diameter of each pipe is most preferably 3 inches and the length is preferably 80 feet. The length of each pipe may be selected according to the space available for the system. The PBR pipes are preferably installed with their orientations horizontal to the ground and are stacked vertically on racks. Vertical spacing between 3-inch diameter PBR pipes is preferably 6 inches on center and the number of pipes on a rack is determined by the residence time required to reduce nutrients and/or trace metals to the desired level. At the end of each PBR pipe is a 180 degree elbow joint that connects vertically adjacent PBR pipes in the rack so that the pipes are connected in series to form a single serpentine path.

A portion of the mixture flow from the manifold preferably enters each PBR at the top pipe of the rack and flows sequentially through all of the PBR pipes. When the mixture flow exits the bottom pipe of the PBR, the desired level of treatment is achieved. Thus, the treatment takes place in a single pass through the PBR and no recycling of the mixture flow through the PBR is needed.

While the mixture flow is traveling through the PBR the pH of the mixture flow is monitored and $CO_2$ is injected automatically using a peristaltic dosing pump 204 (or equivalent) to achieve an appropriate pH level in the PBR, typically a neutral pH in the range of 6.9 to 7.1. The PBR is illuminated by light of appropriate wavelength and with sufficient intensity to facilitate appropriate levels of photosynthesis by the algae in the mixture flow in the PBR. The light may be provided by a natural light source 216 and/or artificial light source 214. In a preferred embodiment, the light preferably includes wavelengths between 550 and 700 nanometers, or more preferably between 650 and 675 nanometers. The ambient intensity from the natural light source may be monitored and the artificial light source intensity may be automatically adjusted to compensate for changing intensity levels of the natural light source. In addition to pH level and light, continuous in-line monitoring of algae density and flow rate are also performed.

In some implementations, the mixture flow is exposed to direct light in the PBR for a duration that is approximately 40% to 60% of the total time that the mixture flow is traveling through the blend, nutrient removal, and separation and solids recovery stages. During the 50% of time in which the mixture flow is not exposed to direct light it is either in the separation stage or in the blend stage.

Retention time, and therefore the length and height of each PBR, is defined as the approximate duration a given particle takes to traverse the PBR from entry at the top to exit at the bottom. The retention time is thus directly related to pipe diameter, total PBR length, and volumetric flow rate. Therefore, the design of the system, and the retention time for the system, is calculated using the known values for estimated available nutrients, total system biomass, average expected growth rate of the selected algae organism and desired nutrient levels when exiting the system, and is customized for each system based on the specific chemistry of the received water being treated and the targeted constituents to be removed.

Upon exiting the bottom of the PBR, the treated mixture flow portion is combined with other treated mixture flow portions that have passed similarly in parallel through other PBRs in the array 212, forming a single treated mixture flow.

Stage 5: Separation, Solids Recovery, and Return of Algae Flow

The treated mixture flow from the PBRs enters diverter (typically an automatic gate or needle valve) 218 which diverts an excess fraction of the mixture flow as waste activated algae (WAA). The amount of WAA that is diverted is, for example, between 2% and 10% of the total system flow rate. The amount of WAA is equivalent to the amount of algae grown in surplus of the identified optimum density. Preferably, the system is customized for a given water effluent by calculating the desired density of the algae culture and the amount of WAA that must be removed on a continual basis to achieve the desired results. The amount of WAA may be calculated using the following primary factors: growth rate of the algae, total system retention time and flow rate. Additional secondary factors that may be accounted for in determining the WAA include, but are not limited to, nutrients in the water effluent, light availability, diameter of pipe size, and water temperature. For example, for an algae growth rate of 1 duplication per 24 hours, the corresponding algae growth is 100%/24 hours=4.16% per hour. For a system retention time of 1 hour, the continual harvest rate of system volume is 1 hour× 4.16%/hour=4.16%.

The portion of mixture flow that is not diverted as WAA continues to a filter equalization tank 220 where associated flow meters and pumps are designed to monitor and maintain a consistent flow into the separation and solids recovery stage of the treatment process.

In alternative embodiments, the WAA may instead be diverted from the RAA flow by positioning diverter 218 downstream from cross-flow filter 222. Such an implementation would apply the same diversion principles as described above. The mixture flow from the PBRs, in such alternative embodiments, would flow directly to a filter equalization tank 220.

After exiting the filter equalization tank 220 the mixture flow enters a separation and solids recovery process which removes solids (algae) from the liquid (water). Upon completion of this stage, the solids in the form of a dense microalgae flow (RAA) are pumped to the blending tank 210 where they are blended with upstream conditioned flow and begin the process of nutrient and/or trace metal removal. Maintaining a continual supply of healthy algae at the optimal density that consistently circulates through blending, PBR, and separation stages provides the ability to treat a continuous flow of water. Preferred embodiments of the invention typically return to the blending tank 210 100% of the dense live microalgae (RAA) flow exiting the separation stage, although it is possible to return less, e.g., 50% or more, such as in alternate embodiments where diverter 218 for WAA is positioned downstream from tank 224, as described earlier.

In a preferred embodiment, the separation and solids recovery process is implemented by pumping the mixture from filter equalization tank 220 through a cross-flow filter 222. Inside the cross-flow filter 222 the mixture flow travels across the surface of a filter membrane at a pressure between 20 and 80 psi to maintain turbulent flow. Maintaining this pressure, with flow meters and pumps, in the cross-flow filter 222 forces a portion of the water in the mixture flow through sub-micron diameter pores of the filter membrane while suspended particulates (i.e., algae) remain in a retentate stream, or RAA. The RAA flow exiting the filter typically has at least twice the density of algae by volume as the mixture flow entering the filter. Water that is forced through the pores of the membrane filter forms a flow of fully treated water and is referred to as the permeate. Embodiments easily achieve permeate flows with less than 50 mg/l microalgae. In a preferred embodiment, the permeate flow has less than 2 mg/l microalgae. The permeate may be discharged into the environment pursuant to appropriate regulations or may be re-used in upstream processes. In some embodiments, the permeate may be further polished prior to discharge or re-use by optional polishing apparatus 226 which performs filtering and disinfection, e.g., by ultra-violet irradiation.

Retentate is pumped from the cross-flow filter 222 to optional RAA equalization tank 224 which is designed to receive and hold RAA in order to ensure consistent flow rate of RAA into the blending tank 210. In embodiments of the invention, a minimum of 50% by volume of the dense live microalgae (RAA) flow is returned via a return line to the blending vessel. More preferably, 99% to 100% by volume of the dense live microalgae flow (RAA) is returned to the blending vessel.

Figure 2B:
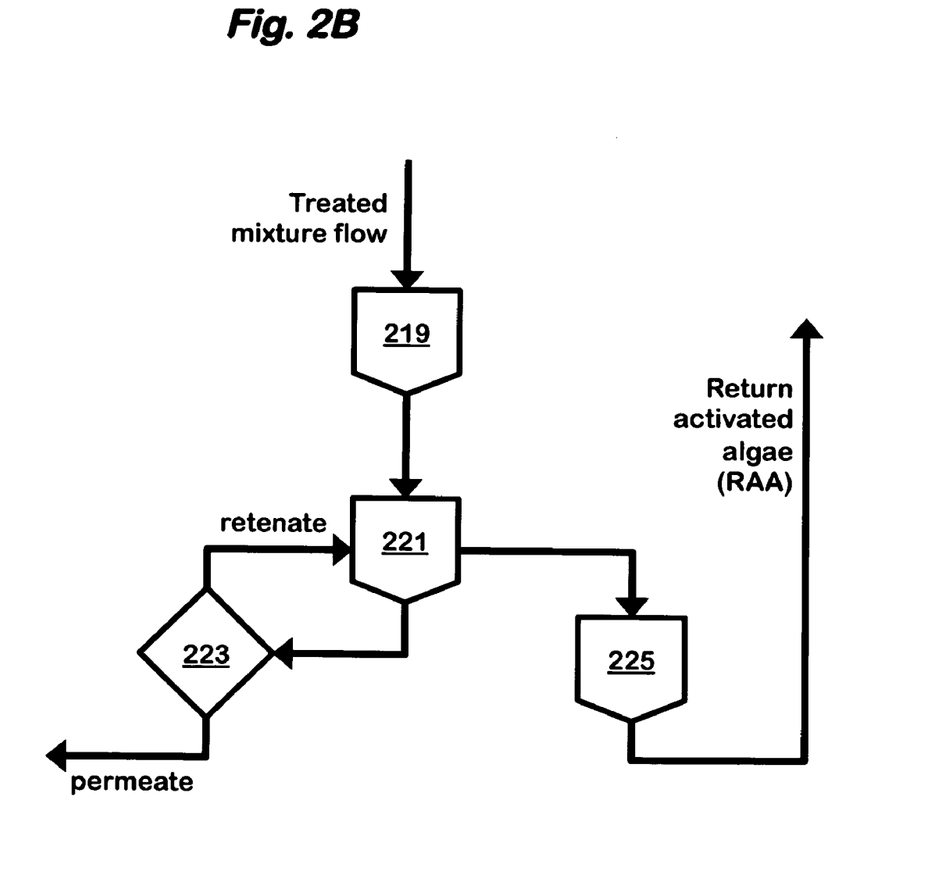
FIG. 2B is a process flow schematic illustrating an alternate embodiment of a separation and solids recovery stage of the process shown in FIG. 2A, according to an embodiment of the invention.

An alternative embodiment of the separation and solids recovery stage is shown in FIG. 2B. In this embodiment, the treated mixture flow is pumped from the filtration equalization tank 219 to a filter condensing tank 221. The mixture in filter condensing tank 221 is then pumped into cross-flow filter 223. In cross-flow filter 223, a filter membrane separates the mixture into a permeate stream and a retentate stream, just as in the embodiment described above. In this case, however, the retentate from the cross-flow filter 223 is circulated back into filter condensing tank 221, increasing the density of algae in the tank. A dense algae flow (RAA) is pumped from filter condensing tank 221 to optional equalization tank 225 prior to being returned to the blending tank upstream. This alternate embodiment is otherwise identical to the embodiment shown in FIG. 2A.

Figure 3:
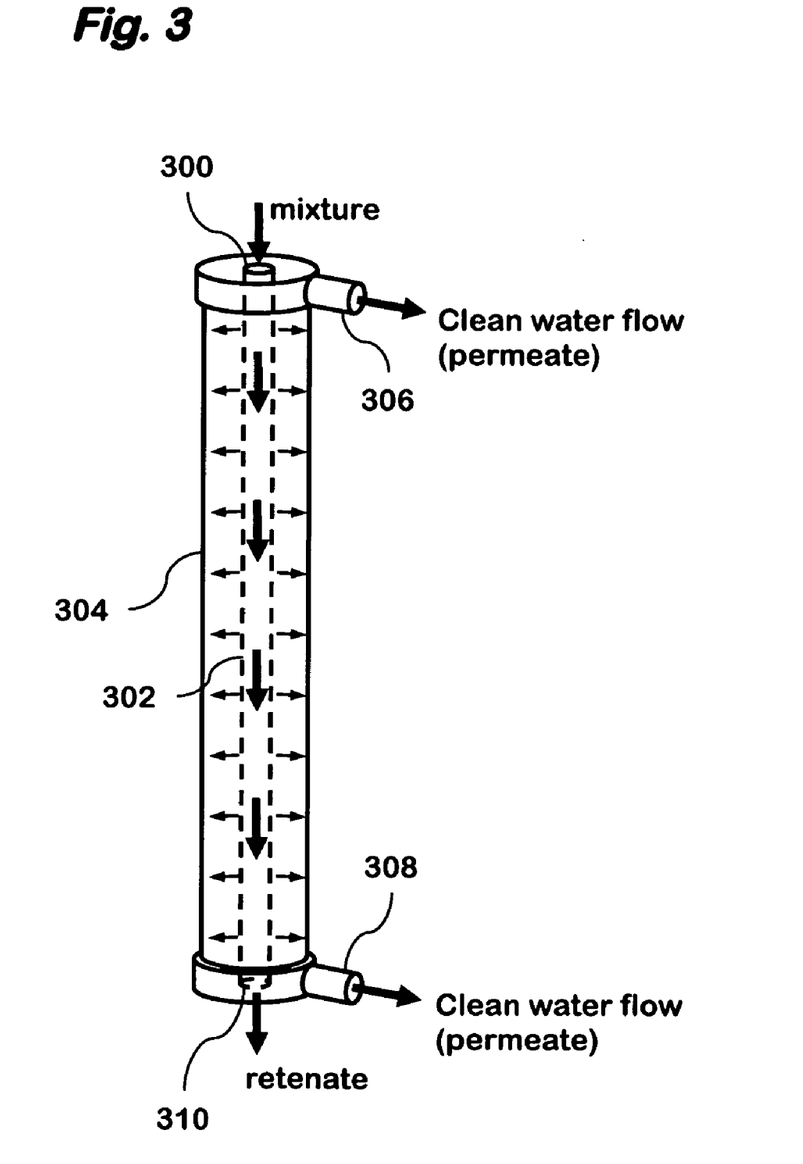
FIG. 3 is a schematic diagram illustrating details of a cross-flow filter used in the system of FIG. 3, according to an embodiment of the invention.

FIG. 3 illustrates the details of a cross-flow filter according to the embodiments described above in relation to FIGS. 2A and 2B. The mixture flow enters the filter at an upper port 300 and flows downward through a 1.5 mm diameter tube 302 enclosed in a cylindrical casing 304. The walls of the tube 302 are made of a membrane (composed, for example, of Polysulfone or Acrylonitrile polymer) with 0.5 micrometer diameter pores. The mixture experiences turbulent flow as it travels downward through the tube 302 at a typical operating pressure between 20 and 80 psi. As a result, a portion of the water in the mixture passes through the membrane walls of the tube 302 and into the space between tube 302 and outer casing 304. This clean water permeate then exits the device through ports 306 and 308 near the top and bottom of the cylindrical casing 304, respectively. Meanwhile, the concentrated algae flow (retentate) exits the filter at a lower port 310. In preferred embodiments, the concentration of algae in the retentate exiting the filter is at least a factor of two greater than the concentration of algae in the mixture entering the filter.

Figure 4A:
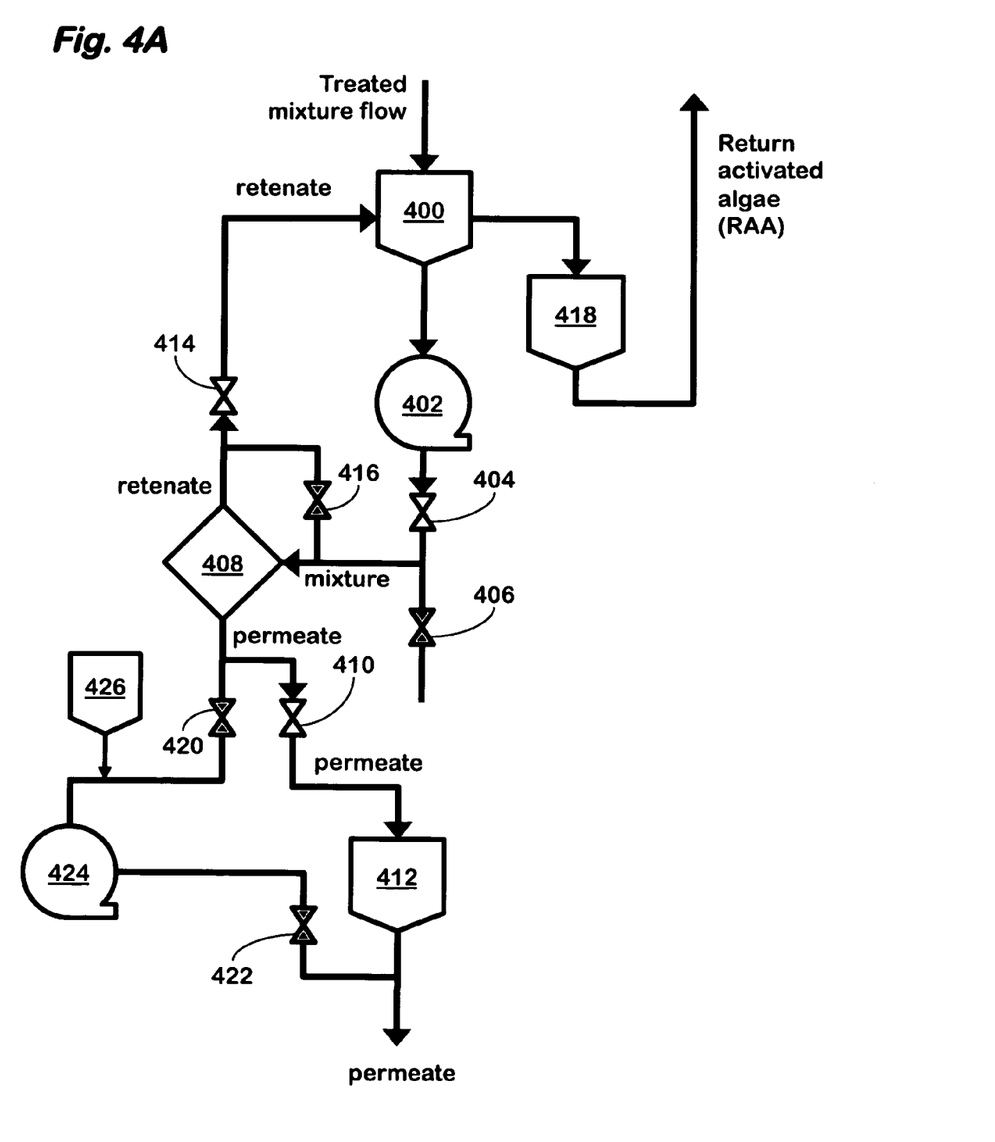
FIG. 4A-B are schematics details associated with the cross-flow filtration and separation stage used in the system of FIG. 3, according to an embodiment of the invention.
Figure 4B:
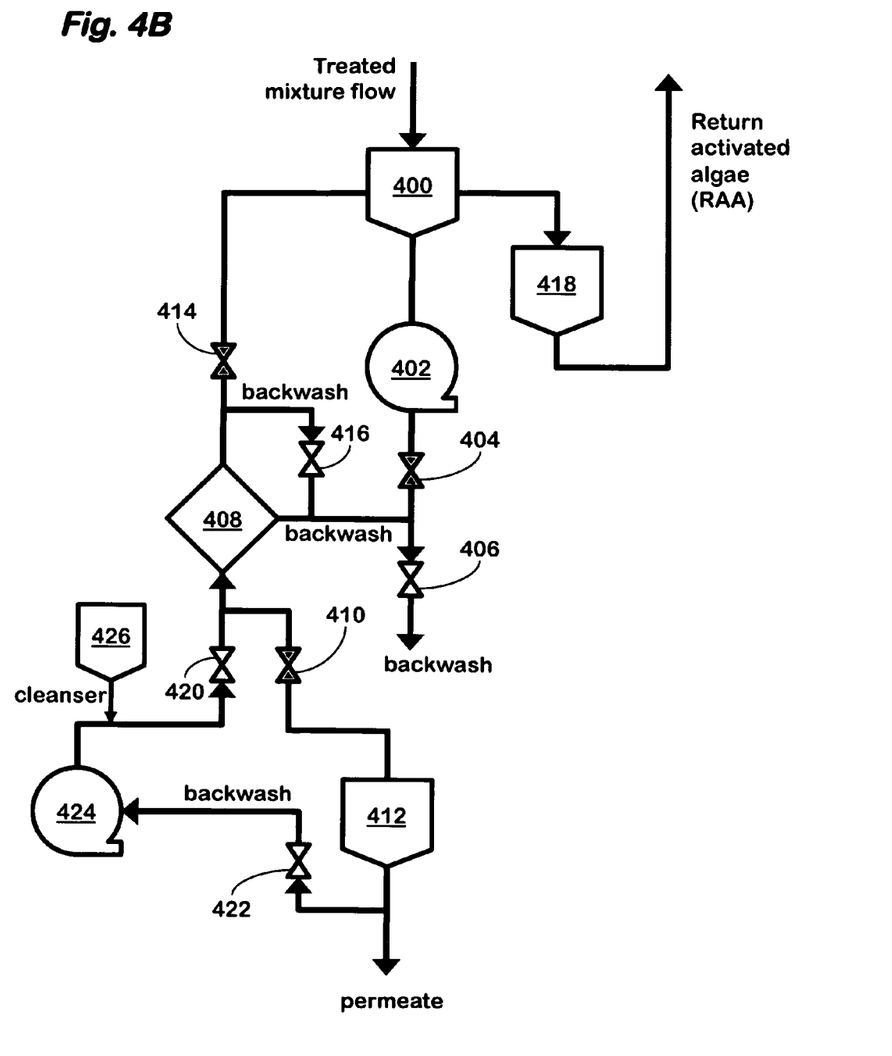

FIGS. 4A-B are schematic illustrations of the detail associated the cross-flow filtration and separation stage in a preferred embodiment which provides for a backwash filter cleaning process, i.e., a clean-in-place (CIP) process. During normal operation, shown in FIG. 4A, the treated mixture flow is pumped from filter equalization tank 400 by pump 402 through valve 404 and into cross-flow filter 408. Pump 402 is controlled by a variable frequency drive (VFD) to provide a constant flow rate that equates to 20 to 80 psi pressure in filter 408. Retentate from the filter 408 passes through valve 414 and cycles back to equalization tank 400. RAA flows from filter equalization tank 400 into RAA equalization tank 418 and then is pumped upstream. Meanwhile, permeate from cross-flow filter 408 flows through valve 410 and into permeate holding tank 412 (optional) and then exits the filtration and separation stage.

During backwash operation, shown in FIG. 4A, valves 406, 416, 420, 422, which were all closed during normal operation, are opened; and valves 404, 410, 414, which were all open during normal operation, are closed. In addition, pump 402, which was on during normal operation, is turned off; and pump 424, which was off during normal operation, is turned on. Consequently, permeate from tank 412 flows through valve 422, pump 424, valve 420, and into cross-flow filter 408 in a reverse flow. Alternatively, an external clean water source may be used for the backwash source instead of water from permeate tank 412. Cleansers 426 may be injected and mixed with the backwash flow prior to entering the cross-flow filter 408. For example, the cleansers may include solvents such as bleach, sodium hypochlorite, or citric acid which help to maintain filter performance. The backwash flow exits the filter 408 through both the mixture input and retentate output. The latter flows through valve 416 and combines with the former, and the combined backwash flow passes through valve 406 and out a disposal line where it is handled according to regulatory and/or any materials safety data sheet (MSDS) requirements. During backwash operation, RAA may continue to flow back from tank 418 and permeate may continue to flow from tank 412. When the backwash mode is completed, the valves and pumps are returned to their normal operating states, as described in reference to FIG. 4A.

The cross-flow filtration subsystem shown in FIGS. 4A-B may be composed of a series of interconnected tubes generally using schedule 80 PVC pipe, pumps, monitoring equipment (i.e. rotometer, restrictor, etc.) and instrumentation for electronic controls and feedback of filtration performance. A series of manual and automated controls including pressure, temperature, and flow gauges may be used to monitor, control and optimize system performance. Data may be constantly acquired through digital telemetry and stored and recorded in a programmable logic controller (PLC). This monitoring and control system may be used to periodically and automatically activate the backwash operation mode and switch back to normal operation. In a preferred embodiment, the backwash mode may be activated for 1 minute out of every 60 minutes.

The invention claimed is:

1. A method for advanced water treatment, the method comprising:
    a) receiving a continuous flow of water;
    b) pre-filtering the received flow of water to reduce suspended solids;
    c) conditioning the pre-filtered flow of water to increase bio-availability of nutrient constituents in the pre-filtered flow;
    d) blending in a blending vessel the conditioned flow with a dense live microalgae flow (RAA) to produce a mixture flow;
    e) passing the mixture flow once through an enclosed tube photobioreactor (PBR) so that microalgae in the mixture flow reproduce and take up nutrients and trace metals in the mixture flow;
    f) continuously separating microalgae from the mixture flow exiting the photobioreactor to produce a treated flow (permeate) and the dense live microalgae flow (RAA) wherein continuously separating of the microalgae comprises filtering the mixture flow exiting the photobioreactor using cross-flow filtration; and
    g) continuously returning the dense live microalgae flow (RAA) to the blending vessel.

2. The method of claim 1 wherein the conditioning is performed in a conditioning tank distinct from the blending vessel.

3. The method of claim 1 wherein the conditioning is performed in the blending vessel.

4. The method of claim 1 further comprising measuring pH of the mixture flow in the photobioreactor and adding $CO_2$ to the photobioreactor based on the measured pH.

5. The method of claim 1 wherein the dense microalgae (RAA) flow contains phototrophic algae selected from the group consisting of *Spirulina, Nannochloropsis, Scenedesmus,* and *Chlamydomonas*.

6. The method of claim 1 further comprising polishing the treated flow (permeate) by filtering.

7. A method for advanced water treatment, the method comprising:
   a) receiving a continuous flow of water;
   b) pre-filtering the received flow of water to reduce suspended solids;
   c) conditioning the pre-filtered flow of water to increase bio-availability of nutrient constituents in the pre-filtered flow;
   d) blending in a blending vessel the conditioned flow with a dense live microalgae flow (RAA) to produce a mixture flow;
   e) passing the mixture flow once through an enclosed tube photobioreactor (PBR) so that microalgae in the mixture flow reproduce and take up nutrients and trace metals in the mixture flow;
   f) continuously separating microalgae from the mixture flow exiting the photobioreactor to produce a treated flow (permeate) and the dense live microalgae flow (RAA); and
   g) continuously returning the dense live microalgae flow (RAA) to the blending vessel;
   further comprising removing from the prefiltered flow total suspended solids and tannins (color).

8. A method for advanced water treatment, the method comprising:
   a) receiving a continuous flow of water;
   b) pre-filtering the received flow of water to reduce suspended solids;
   c) conditioning the pre-filtered flow of water to increase bio-availability of nutrient constituents in the pre-filtered flow;
   d) blending in a blending vessel the conditioned flow with a dense live microalgae flow (RAA) to produce a mixture flow;
   e) passing the mixture flow once through an enclosed tube photobioreactor (PBR) so that microalgae in the mixture flow reproduce and take up nutrients and trace metals in the mixture flow;
   f) continuously separating microalgae from the mixture flow exiting the photobioreactor to produce a treated flow (permeate) and the dense live microalgae flow (RAA); and
   g) continuously returning the dense live microalgae flow (RAA) to the blending vessel;
   further comprising sterilizing the prefiltered flow with UV irradiation.

9. A method for advanced water treatment, the method comprising:
   a) receiving a continuous flow of water;
   b) pre-filtering the received flow of water to reduce suspended solids;
   c) conditioning the pre-filtered flow of water to increase bio-availability of nutrient constituents in the pre-filtered flow;
   d) blending in a blending vessel the conditioned flow with a dense live microalgae flow (RAA) to produce a mixture flow;
   e) passing the mixture flow once through an enclosed tube photobioreactor (PBR) so that microalgae in the mixture flow reproduce and take up nutrients and trace metals in the mixture flow;
   f) continuously separating microalgae from the mixture flow exiting the photobioreactor to produce a treated flow (permeate) and the dense live microalgae flow (RAA); and
   g) continuously returning the dense live microalgae flow (RAA) to the blending vessel;
   further comprising measuring pH levels of the prefiltered flow and adding $CO_2$ to the pretreated flow based on the measured pH levels.

10. A method for advanced water treatment, the method comprising:
    a) receiving a continuous flow of water;
    b) pre-filtering the received flow of water to reduce suspended solids;
    c) conditioning the pre-filtered flow of water to increase bio-availability of nutrient constituents in the pre-filtered flow;
    d) blending in a blending vessel the conditioned flow with a dense live microalgae flow (RAA) to produce a mixture flow;
    e) passing the mixture flow once through an enclosed tube photobioreactor (PBR) so that microalgae in the mixture flow reproduce and take up nutrients and trace metals in the mixture flow;
    f) continuously separating microalgae from the mixture flow exiting the photobioreactor to produce a treated flow (permeate) and the dense live microalgae flow (RAA); and
    g) continuously returning the dense live microalgae flow (RAA) to the blending vessel;
    further comprising measuring nutrient levels of the conditioned flow and adding nutrients to the conditioned flow based on the measured nutrient levels.

11. A method for advanced water treatment, the method comprising:
    a) receiving a continuous flow of water;
    b) pre-filtering the received flow of water to reduce suspended solids;
    c) conditioning the pre-filtered flow of water to increase bio-availability of nutrient constituents in the pre-filtered flow;
    d) blending in a blending vessel the conditioned flow with a dense live microalgae flow (RAA) to produce a mixture flow;
    e) passing the mixture flow once through an enclosed tube photobioreactor (PBR) so that microalgae in the mixture flow reproduce and take up nutrients and trace metals in the mixture flow;
    f) continuously separating microalgae from the mixture flow exiting the photobioreactor to produce a treated flow (permeate) and the dense live microalgae flow (RAA); and
    g) continuously returning the dense live microalgae flow (RAA) to the blending vessel;
    further comprising measuring trace metal levels of the conditioned flow and adding trace metals to the conditioned flow based on the measured trace metal levels.

12. A method for advanced water treatment, the method comprising:
    a) receiving a continuous flow of water;
    b) pre-filtering the received flow of water to reduce suspended solids;
    c) conditioning the pre-filtered flow of water to increase bio-availability of nutrient constituents in the pre-filtered flow;
    d) blending in a blending vessel the conditioned flow with a dense live microalgae flow (RAA) to produce a mixture flow;

e) passing the mixture flow once through an enclosed tube photobioreactor (PBR) so that microalgae in the mixture flow reproduce and take up nutrients and trace metals in the mixture flow;

f) continuously separating microalgae from the mixture flow exiting the photobioreactor to produce a treated flow (permeate) and the dense live microalgae flow (RAA); and g) continuously returning the dense live microalgae flow (RAA) to the blending vessel;

further comprising measuring an ambient light level near the photobioreactor and exposing the photobioreactor to supplemental light, where the amount of supplemental light is based on the measured ambient light level.

13. A method for advanced water treatment, the method comprising:

a) receiving a continuous flow of water;

b) pre-filtering the received flow of water to reduce suspended solids;

c) conditioning the pre-filtered flow of water to increase bio-availability of nutrient constituents in the pre-filtered flow;

d) blending in a blending vessel the conditioned flow with a dense live microalgae flow (RAA) to produce a mixture flow;

e) passing the mixture flow once through an enclosed tube photobioreactor (PBR) so that microalgae in the mixture flow reproduce and take up nutrients and trace metals in the mixture flow;

f) continuously separating microalgae from the mixture flow exiting the photobioreactor to produce a treated flow (permeate) and the dense live microalgae flow (RAA); and g) continuously returning the dense live microalgae flow (RAA) to the blending vessel;

further comprising measuring turbidity of the mixture flow exiting the photobioreactor and removing a fraction of the mixture flow (referred to as WAA flow) from the mixture flow, where the size of the fraction is based on the measured turbidity.

14. A system for advanced water treatment, the system comprising:

a pre-filter for reducing suspended solids from a received flow of water to produce a pre-filtered flow;

a conditioning vessel coupled to the pre-filter for increasing bio-availability of nutrient constituents in a pre-filtered flow to produce a conditioned flow;

a blending vessel coupled to the conditioning vessel for mixing the conditioned flow with a dense live microalgae flow (RAA) to produce a mixture flow;

a dosing device coupled to a transit line connecting the conditioning vessel to the blending vessel for injecting trace metals into the conditioned flow to achieve a desired trace metal level;

an enclosed tube photobioreactor (PBR) coupled to the blending vessel for receiving the mixture flow and allowing microalgae in the mixture flow to reproduce and take up nutrients and trace metals in the mixture flow to produce a treated mixture flow;

a separation filter coupled to the enclosed tube photobioreactor for continuously separating microalgae from the treated mixture flow exiting the photobioreactor to produce a clean water flow (permeate) and the dense live microalgae flow (RAA); and a dense live microalgae flow (RAA) return coupled to the separation filter for continuously returning the dense live microalgae flow (RAA) to the blending vessel.

* * * * *